(12) United States Patent
Myerson et al.

(10) Patent No.: US 7,411,061 B2
(45) Date of Patent: *Aug. 12, 2008

(54) METHOD OF SYNTHESIZING POLYNUCLEOTIDES USING IONIC LIQUIDS

(75) Inventors: Joel Myerson, Berkeley, CA (US); Michel G. M. Perbost, Bethany, CT (US); Douglas J. Dellinger, Boulder, CO (US); Geraldine F Dellinger, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 11/020,408

(22) Filed: Dec. 22, 2004

(65) Prior Publication Data

US 2005/0106685 A1    May 19, 2005

Related U.S. Application Data

(63) Continuation of application No. 09/999,623, filed on Oct. 31, 2001, now Pat. No. 6,858,720.

(51) Int. Cl.
*C07H 21/00* (2006.01)
*C07H 21/02* (2006.01)
*C07H 21/04* (2006.01)

(52) U.S. Cl. ............... 536/25.3; 536/25.33; 536/25.34; 536/22.1; 536/23.1; 536/25.41

(58) Field of Classification Search .................. None
See application file for complete search history.

(56) References Cited

U.S. PATENT DOCUMENTS

| | | | |
|---|---|---|---|
| 6,022,963 | A | 2/2000 | McGall et al. |
| 6,069,243 | A | 5/2000 | Scozzari |
| 6,222,030 | B1 | 4/2001 | Dellinger et al. |
| 6,242,266 | B1 | 6/2001 | Schleifer et al. |
| 6,274,725 | B1 | 8/2001 | Sanghvi et al. |
| 6,852,850 | B2 * | 2/2005 | Myerson et al. ............. 536/25.3 |
| 6,858,720 | B2 * | 2/2005 | Myerson et al. ............. 536/25.3 |

FOREIGN PATENT DOCUMENTS

| | | |
|---|---|---|
| EP | 0742287 A2 | 9/1996 |
| WO | WO96/28457 | 9/1996 |
| WO | WO98/39348 | 3/1998 |
| WO | WO99/54509 | 4/1998 |
| WO | WO00/18778 | 9/1998 |
| WO | WO00/31/594 | 4/2000 |

OTHER PUBLICATIONS

Serge L. Beaucage and Radhakrishnan P. Iyer, "Advances in the Synthesis of Oligonucleotides by the Phosphoramidite Approach"; Tetrahedron Report No. 309, Vo. 48, No. 12, pp. 2223-2313, 1992.
Ahmad Hasan, Hong Li, Jeno Toamsz and Barbara Ramsay Shaw; "Base-boronated Dinucleotides: synthesis and effect of N7-cyanoborane substitution on the base protons"; Nucleic Acids Research, 1996 vol. 24, No. 11; pp. 2150-2157.
Frank Bergman, Erich Kueng, Patrick Iaiza, and Willi Bannwarth; Allyl as Internucleotide Protecting Group in DNA Synthesis to be cleaved off by Ammonia; Tetrahedron, vol. 51, No. 25, 99. 6971-6976, 1995.
Frank Bergman and Wolfgang Pfleiderer; "Nucleotides"; The 2-Dansylethoxycarbonyl (=2-{[5-(Dimethylamino)napththalen-1-yl]sulfonyl} ethoxcarbonyl; Dnseoc) Group for Protection of the 5'-Hydroxy Function in Ologodeoxyribonucleotide Synthesis; Helvetica Chimica Acta—vol. 77(1994); pp. 203-213.
Michael C. Pirrung and Lora Fallon; Glenn McGall "Proofing of Photolithographic DNA Synthesis with 3' , 5' -Dimethoxybenzoinyloxycarbonyl-Protected Doxynucleoside Phosphoramidites"; 1998 American Chemical Society, pp. 241-246.
Haroald Sigmund, Thomas Maier and Wolfgang Pfeiderer; A New Type of Fluorescence Labeling of Nucleosides Nucleotides and Oligonucleotides:; Nucleosides & Nucleotides, 16(5&6), pp. 685-696 (1997).
Glenn H. McGall, Anthony D. Barone, Martin Diggelman, Stephen P. A. Fodor, Erik Gentalen, and Nam Ngo; "The Efficiency of Light-Directed Synthesis of DNA Arrays on Glass Substrates"; Journal of the American Chemical Society, vol. 119, No. 22, Jun. 4, 1997, pp. 5081-5090.
Michael C. Pirrung and Jean Claude-Bradley; "Comparison of Methods for Photochemical Phosphoramidite-Based DNA Synthesis", J. Org. Chem. 1995, vol. 60, pp. 6270-6276.
Hayes Dougan, John B. Hobbs, Jeffrey I. Weitz and Donald M. Lyster; "Sunthesis and Raioiodination of a Stannyl Oligofeoxyribonucleotide"; Nucleic Acids Research, 1997, vol. 25, No. 14, pp. 2897-2901.

(Continued)

*Primary Examiner*—Shaojia Anna Jiang
*Assistant Examiner*—Traviss C McIntosh, III

(57) ABSTRACT

A method of synthesizing polynucleotides is disclosed. The method involves contacting a first nucleotide with a selected reactive group in the presence of an ionic liquid. The selected reactive group may be on a second nucleotide, a polynucleotide, or on a moiety on an insoluble substrate, for example in an oligonucleotide synthesizer.

24 Claims, 1 Drawing Sheet

OTHER PUBLICATIONS

Shegenori Iwai and Eiko Ohtsuka; "t'-Levulinyl and 2-tetrahydrofuranyl protection for the synthesis of oligoribonucleotides by the Phosphoramidite approach"; Nucleic Acids Research, vol. 16, No. 20, 1988.

Earle et al., "Ionic Liquids, Green solvents for the future", Pure Applied Chemistry, vol. 72, No. 7, pp. 1391-1398, 2000.

Earle et al., Paradigm Confirmed: The First Ude of Ionic Liquids to Dramatically Influence the Outcome of Chemical Reactions Organic Letters, vol. 6, No. 5, pp. 707-710, 2004.

* cited by examiner

METHOD OF SYNTHESIZING POLYNUCLEOTIDES USING IONIC LIQUIDS

CROSS-REFERENCE TO RELATED APPLICATION

This is a Continuation of application Ser. No. 09/999,623, filed on Oct. 31, 2001, now U.S. Pat. No. 6,858,720, the entire disclosure of which is incorporated herein by reference.

DESCRIPTION

1. Field of the Invention

The invention relates generally to methods of polynucleotide synthesis. The invention more specifically relates to forming internucleotide bonds in a solution containing ionic liquid.

2. Background of the Invention

Much interest has been focused on reactions for coupling nucleotides to form polynucleotide chains, and various chemical schemes have been described for the synthesis of polynucleotides. Typically these methods use a nucleoside reagent of the formula:

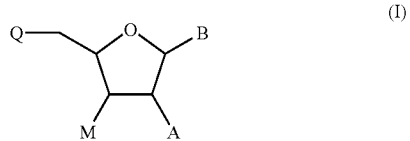

in which:

A represents H or an optionally protected hydroxyl group;

B is a purine or pyrimidine base whose exocyclic amine functional group is optionally protected;

one of M or Q is a conventional protective group for the 3' or 5'-OH functional group while the other is:

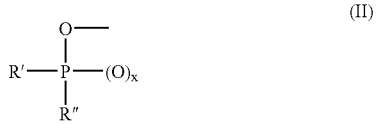

where x may be 0 or 1, provided that:

a) when x=1:

R' represents H and R" represents a negatively charged oxygen atom; or

R' is an oxygen atom and R" represents either an oxygen atom or an oxygen atom carrying a protecting group; and b) when x=0, R' is an oxygen atom carrying a protecting group and R" is either a hydrogen or a di-substituted amine group.

When x is equal to 1, R' is an oxygen atom and R" is an oxygen atom, the method is in this case the so-called phosphodiester method; when R" is an oxygen atom carrying a protecting group, the method is in this case the so-called phosphotriester method.

When x is equal to 1, R' is a hydrogen atom and R" is a negatively charged oxygen atom, the method is known as the H-phosphonate method.

When x is equal to 0, R' is an oxygen atom carrying a protecting group and R" is a halogen, the method is known as the phosphite method, and when R" is a leaving group of the disubstituted amine type, the method is known as the phosphoramidite method.

The conventional sequence used to prepare an oligonucleotide using reagents of the type of formula (I), basically follows four separate steps: (a) coupling a selected nucleoside which also has a protected hydroxy group, through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing methods of preparing polynucleotides are well known and described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives, CRC Press, Boca Raton, Fla., pages 100 et seq., U.S. Pat. Nos. 4,415,732, 4,458,066, 4,500,707, 5,153,319, 5,869,643, EP 0294196, and elsewhere. The phosphoramidite and phosphite triester approaches are most broadly used, but other approaches include the phosphodiester approach, the phosphotriester approach and the H-phosphonate approach. Such approaches are described in Beaucage et al., Tetrahedron (1992) 12:2223-2311. A more recent approach for synthesis of polynucleotides is described in U.S. Pat. No. 6,222,030 B1 to Dellinger et al, Issued Apr. 24, 2001.

In the typical phosphoramidite method of solid phase oligonucleotide synthesis, the synthesis typically proceeds in the 3' to 5' direction (referring to the sugar component of the added nucleoside), although the synthesis may easily be conducted in the reverse direction. The added nucleoside generally has a dimethoxytrityl protecting group on its 5' hydroxyl and a phosphoramidite functionality on its 3' hydroxyl position. Beaucage et al. (1981) Tetrahedron Lett. 22:1859. See FIG. 1 for a schematic representation of this technology. In FIG. 1 "B" represents a purine or pyrimidine base, "DMT" represents dimethoxytrityl protecting group and "iPr" represents isopropyl. In the first step of the synthesis cycle, the "coupling" step, the 5' end of the growing chain is coupled with the 3' phosphoramidite of the incoming monomer to form a phosphite triester intermediate (the 5' hydroxyl protecting group prevents more than one monomer per synthesis cycle from attaching to the growing chain). Matteucci et al. (1981) J. Am. Chem. Soc. 103:3185. Next, the optional "capping reaction" is used to stop the synthesis on any chains having an unreacted 5' hydroxyl, which would be one nucleotide short at the end of synthesis. The phosphite triester intermediate is subjected to oxidation (the "oxidation" step) after each coupling reaction to yield a more stable phosphotriester intermediate. Without oxidation, the unstable phosphite triester linkage would cleave under the acidic conditions of subsequent synthesis steps. Letsinger et al. (1976) J. Am. Chem. Soc. 98:3655. Removal of the 5' protecting group of the newly added monomer (the "deprotection" step) is typically accomplished by reaction with acidic solution to yield a free 5' hydroxyl group, which can be coupled to the next protected nucleoside phosphoramidite. This process is repeated for each monomer added until the desired sequence is synthesized.

According to some protocols, the synthesis cycle of couple, cap, oxidize, and deprotect is shortened by omitting the capping step or by taking the oxidation step 'outside' of the cycle and performing a single oxidation reaction on the completed chain. For example, oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

Conventional synthesis protocols of oligonucleotides are not without disadvantages. For example, cleavage of the DMT protecting group under acidic conditions gives rise to the resonance-stabilized and long-lived bis(p-anisyl)phenylmethyl carbocation. Gilham et al. (1959) J. Am. Chem. Soc. 81:4647 Protection and deprotection of hydroxyl groups with DMT are thus readily reversible reactions, resulting in side reactions during oligonucleotide synthesis and a lower yield than might otherwise be obtained. To circumvent such problems, large excesses of acid are used with DMT to achieve quantitative deprotection. As bed volume of the polymer is increased in larger scale synthesis, increasingly greater quantities of acid are required. The acid-catalyzed depurination which occurs during the synthesis of oligodeoxyribonucleotides is thus increased by the scale of synthesis. Caruthers et al., in Genetic Engineering: Principles and Methods, J. K. Setlow et al., Eds. (New York: Plenum Press, 1982). Solvent use in larger scale synthesis becomes increasingly prohibitive as well, as more washing is required. In particular, the reagents used in the coupling step typically are highly susceptible to hydrolysis, which requires dry solvents, further increasing the cost of solvents.

Salts that are fluid at room temperature have been investigated as environmentally friendly solvents. These salts have been termed 'room temperature ionic liquids' (herein simply referred to as 'ionic liquids') and are generally composed of a heterocyclic cation, e.g. a substituted imidazole or pyridine, and an anion such as tetrafluoroborate or hexafluorophosphate, although certain organic anions such as methylsulfate ($CH_3SO_4^-$), among others, have been discovered to be effective as the anion in certain organic liquids. Ionic liquids are known to dissolve a wide range of substances, both organic and inorganic. Ionic liquids typically are non-corrosive, have little or no vapor pressure under standard conditions, and exhibit low viscosity. More information regarding ionic liquids may be gleaned from two review articles by Hussey (Hussey, C. L., Adv. Molten Salt Chem. (1983) 5:185; and Hussey, C. L., Pure Appl. Chem. (1988) 60:1763).

SUMMARY OF THE INVENTION

The invention is thus addressed to the aforementioned deficiencies in the art, and provides a novel method for synthesizing oligonucleotides, wherein the method has numerous advantages relative to prior methods such as those discussed above. The method involves forming an internucleotide bond between a first nucleoside moeity and a second nucleoside moiety in an environment that includes an ionic liquid.

In a preferred embodiment of the invention, the second nucleoside moiety is immobilized to an insoluble substrate. The second nucleoside moiety on the insoluble substrate is contacted with a solution having the first nucleoside moiety in a solution containing ionic liquid. An internucleoside bond is thus formed between the first and second nucleoside moieties. The product of the reaction is a polynucleotide wherein the first and second nucleoside moieties have been bonded together.

In some embodiments, the first nucleoside moiety corresponds to a nucleoside phosphoramidite monomer, as in conventional polynucleotide synthesis as described above. The invention also encompasses the formation of an internucleoside bond between two polynucleotides or oligonucleotides, or between a polynucleotide and an oligonucleotide. In such case, the first nucleoside moiety corresponds to the one of the polynucleotides or oligonucleotides, and the second polynucleotide moiety corresponds to the polynucleotide or oligonucleotide to be joined to the first nucleoside moiety.

In particular embodiments, the reaction is geared to producing "native" polynucleotides, i.e. substantially identical to those that might be isolated from nature. In other embodiments, the reaction is used to synthesize polynucleotide analogues, which may have 'modified' (not occurring in nature) phosphodiester backbones or modified bases attached to the sugar groups in the phosphodiester backbones.

In another embodiment, after the internucleotide bond has been formed, it is modified, e.g. by oxidation, to form the ultimate polynucleotide product. The present invention in its broadest sense encompasses materials and methods for use in forming polynucleotides, polynucleotide intermediates, and polynucleotide analogues. The invention also encompasses reagents and methods for synthesis of oligonucleotides allowing the synthesis to be conducted under a wide range of conditions and allowing for the use of a variety of protecting groups. This wide range includes the use of co-solvents along with the ionic liquid in the coupling reaction.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates a prior art oligonucleotide synthesis method using phosphoramidite monomers. The known prior art methods, including the one illustrated, do not describe the use of ionic liquids in the coupling step where the internucleotide bond is formed.

DETAILED DESCRIPTION

Figure 1:
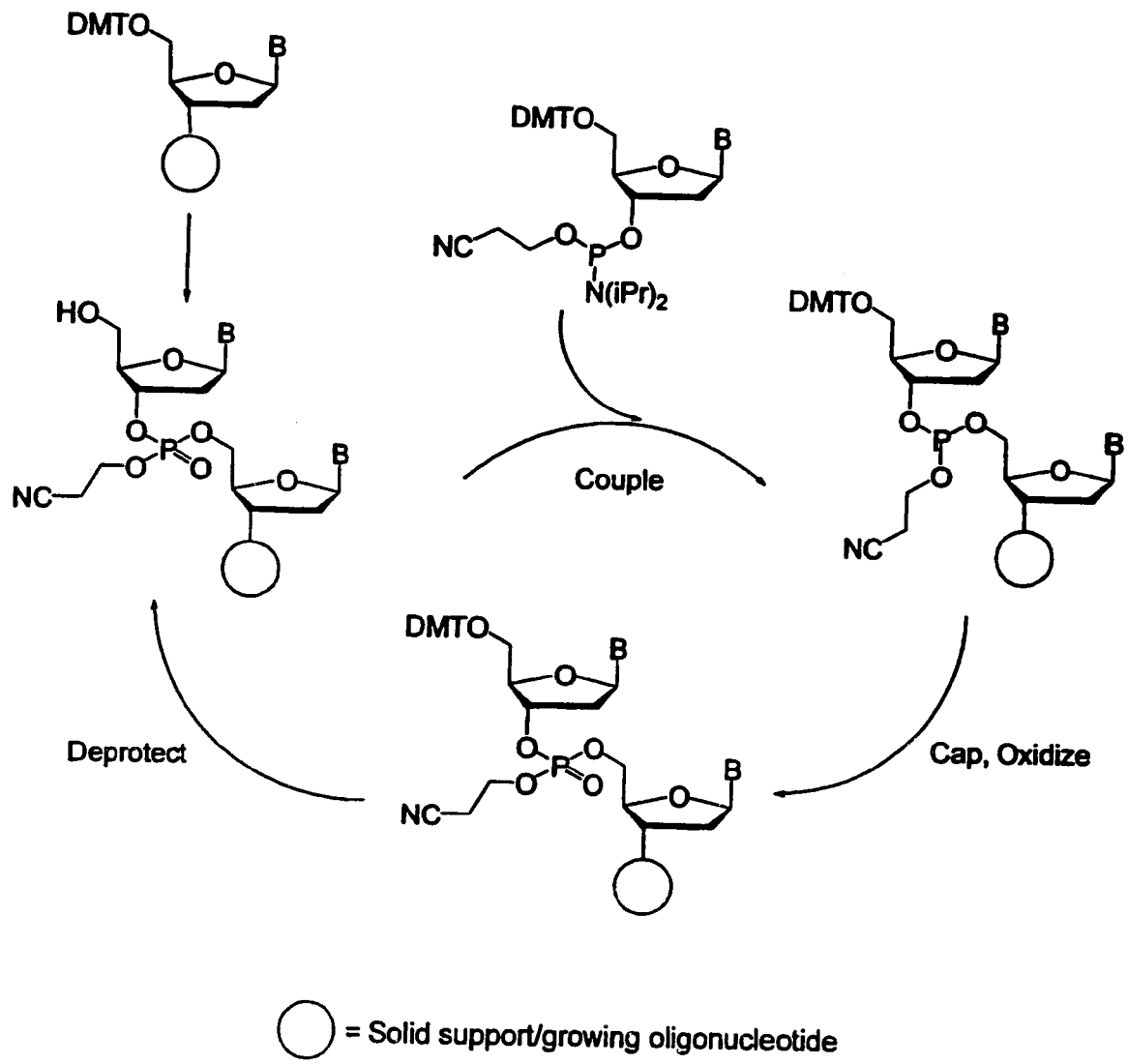

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise Thus, for example, reference to "an insoluble support" includes a plurality of insoluble supports. In this specification and in the claims that follow, reference will be made to a number of terms that shall be defined to have the following meanings unless a contrary intention is apparent:

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone, e.g with a modified sugar group, or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base. A "nucleoside moiety" refers to a molecule having a sugar group and a nitrogen containing base (as in a nucleoside) as a portion of a larger molecule, such as in a polynucleotide, oligonucleotide, or nucleoside phosphoramidite. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which isoxidized to a phosphate in a later step in the synthesis, or a protected polynucleotide which is then deprotected. An "oligonucleotide" generally refers to a nucleotide multimer of about 2 to 100 nucleotides in length, while a "polynucleotide" includes a nucleotide multimer having any number of nucleotides. It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladerline, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "intemucleotide bond" refers to a chemical linkage between two nucleoside moieties, such as a phosphodiester linkage in nucleic acids found in nature, or such as linkages well known from the art of synthesis of nucleic acids and nucleic acid analogues. An intemucleotide bond may comprise a phospho or phosphite group, and may include linkages where one or more oxygen atoms of the phospho or phosphite group are either modified with a substituent or replaced with another atom, e.g. a sulfur atom, or the nitrogen atom of a mono- or di-alkyl amino group.

A "group" includes both substituted and unsubstituted forms. Typical substituents include one or more lower alkyl, any halogen, hydroxy, or aryl, or optionally substituted on one or more available carbon atoms with a nonhydrocarbyl substituent such as cyano, nitro, halogen, hydroxyl, or the like. Any substituents are typically chosen so as not to substantially adversely affect reaction yield (for example, not lower it by more than 20% (or 10%, or 5% or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

A "protecting group" is used in the conventional chemical sense to reference a group which reversibly renders unreactive a functional group under specified conditions of a desired reaction. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. A "hydroxyl protecting group" refers to a protecting group where the protected group is a hydroxyl. A "reactive-site hydroxyl" is the terminal 59hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions. Preferred protecting groups that are capable of removal under acidic conditions ("acid-labile protecting groups") include those such as tetrahydropyranyl groups, e.g. tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. A trityl group is a triphenylmethyl group. Suitable protecting groups are described in "Protective Groups in Organic Synthesis" by T. W. Green, Wiley Interscience.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cycloliexyl, 3-methylpentyl, 2,2-dimethylbutyl, and 2,3-dimethylbutyl. The term "lower alkyl" intends an alkyl group of one to eight carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic: alkyl groups such as cyclopropyl, cyclobutyl, cyclopentyl, cyclohexyl, cycloheptyl and cyclooctyl.

The term "alkenyl" as used herein, unless otherwise specified, refers to a branched, unbranched or cyclic (in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl arid allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

The synthesis of polynucleotides has been well-studied, and methods incorporate both aqueous and organic solvents. It is well known that changing the solvent in a reaction system frequently affects the performance of the reaction, sometimes profoundly. The ionic nature of ionic liquids fundamentally differs from molecular nature of aqueous or organic solvents used in various steps of the polynucleotide synthesis cycle. Potential problems include changes of chemical mechanism, possibly favoring different products due to the ionic nature of the solvent. Stabilization of charged reaction intermediates due to interaction with the ionic liquid, or chemical reaction with components of the ionic liquid itself might be expected. Will the short-lived reaction intermediates found in conventional solvents be long-lived stable intermediates in an ionic liquid? Will changes in the relative stabilities of reaction intermediates change the available reaction pathways? Will the expected changes in reaction kinetics shift the balance between thermodynamic and kinetic control, and hence produce different products?

We determined to study the effect of the coupling reaction in ionic liquid solvent as an alternative to molecular solvents (aqueous and organic solvents). We have discovered that, despite the previously mentioned potential problems, we were able to achieve coupling of nucleoside moieties via formation of an internucleotide bond in ionic liquids. We have now found that various advantages exist in performing the coupling reaction in ionic liquids. One advantage we found was that the hydrophobicity of ionic liquid led to reduced problems in dealing with hydrolysis of the reactants due to water in the reaction environment Less solvent may be used to wash in between coupling steps, and ionic liquid solvents may be recovered more easily, when compared to prior art methods. This may be particularly useful in large scale synthesis, where lots of washing and solvents are required.

Particularly useful phosphoramidites, their preparation, and their use are described in detail in U.S. Pat. Nos. 5,902,878; 5,700,919; 4,668,777; 4,415,732; PCT publication WO 98/41531 and the references cited therein, among others.

The chemical synthesis of thymidine-thymidylate dimers in ionic liquid were preformed by the following protocol:

3 Å molecular sieves were activated by drying in a vacuum oven at 200° C. overnight. A small number of sieves were placed in a 5 ml, round bottom flask with a 14/20 ground glass joint that was then sealed with a rubber septum. 3 ml of 1-ethyl-3-methyl-1H-imidazolium trifluoromethane-sulfonate (Aldrich Chemical Company, Milwaukee, Wis. USA) was added to the flask and the liquid allowed to dry overnight. 5'-Dimethoxytrityl-2'-deoxyThymidine, 3'-[(2-cyanoethyl)-(N,N-diisopropyl)]-phosphoramidite, 0.38 grams, 0.5 mmol, was added to the flask and the solution shaken until the reagent had dissolved. A small amount of the solution was removed from the flask and placed in an NMR tube for analysis by $^{31}$P NMR using an external lock. The resulting NMR spectrum showed the presence of the starting material nucleoside phosphoramidite at δ 147.18 ppm relative to phosphoric acid.

3'-Acetyl Thymidine (ChemGenes Corp., Waltham Mass. USA) 0.14 grams, 0.5 mmol was added to the mixture along with tetrazole 0.18 grams, 2.5 mmol. The solution was shaken on a wrist action shaker until the reagents were completely dissolved. An aliquot of the-reaction mixture was removed from the flask and placed in an NMR tube for analysis by $^{31}$P NMR using an external lock. The resulting NMR spectrum showed complete conversion of the starting material nucleoside phosphoramidite at δ 147.18 ppm to the phosphite triester at δ 139.16 ppm.

In another example, 3 Å molecular sieves were activated by drying in a vacuum oven at 200° C. overnight. A small number of sieves were placed in a 5 ml, round bottom flask with a 14/20 ground glass joint that was then sealed with a rubber septum. In this example, 3 ml of 1-butyl-3-methyl-imidazolium tetrafluoroborate (Solvent Innovation GmbH, 50679 Köln, Germany) was added to the flask and the liquid allowed to dry overnight. 5'-Dimethoxytrityl-2'-deoxyThymidine, 3'-[(2-cyanoethyl)-(N,N-diisopropyl)]-phosphoramidite, 0.38 grams, 0.5 mmol, was added to the flask and the solution shaken until the reagent had dissolved. A small amount of the solution was removed from the flask and placed in an NMR tube for analysis by $^{31}$P NMR using an external lock. The resulting NMR spectrum showed the presence of the starting material nucleoside phosphoramidite at δ 146.94 ppm relative to phosphoric acid.

3'-Acetyl Thymidine (ChemGenes Corp., Waltham Mass.) 0.14 grams, 0.5 mmol was added to the mixture along with tetrazole 0.18 grams, 2.5 mmol. The solution was shaken on a wrist action shaker until the reagents were completely dissolved. An aliquot of the reaction mixture was removed from the flask and placed in an NMR tube for analysis by $^{31}$P NMR using an external lock, The resulting NMR spectrum showed complete conversion of the starting material nucleoside phosphoramidite at δ 146.94 ppm to the phosphite triester diastereomers centered at δ 138.98 ppm.

In general, the product of the coupling reaction, when performed in a solid phase system, may be represented by the following structural formula:

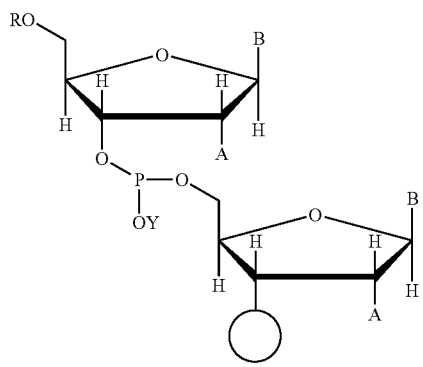

(III)

Wherein:

○ represents the solid support or a support-bound oligonucleotide chain;

A represents H or an optionally protected hydroxyl group;

B is a purine or pyrimidine base whose exocyclic amine functional group is optionally protected; and R is a suitable protecting group, "Y" is hydrido or hydrocarbyl, typically alkyl, alkenyl, aryl, aralkyl, or cycloalkyl. Preferably, Y represents: lower alkyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Most preferably, Y represents methyl, β-cyanoethyl, or 4-nitrophenylethyl.

In this formula, the sugar and the base to the 5' side of the phosphorus atom (P) corresponds to one nucleoside moiety, and the sugar and the base to the 3' side of the phosphorus atom (P) correspond to the other nucleoside moiety.

Ionic liquids that may be used include organic salts that are fluid below about 80° C. at around normal atmospheric pressure (about 1 atmosphere at sea level). The organic salts generally have an organic cation and either an inorganic or organic counterion. The organic cation is preferably an N-substituted pyridine having the following structure:

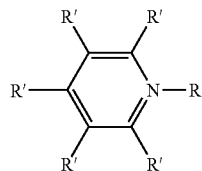

(IV)

wherein R is alkyl and each R' is independently selected from hyrido, alkyl, or halogen;

or a 1,3 di-substituted imidazole having the following structure:

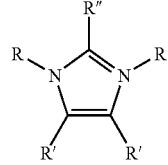

(V)

wherein each R is independently selected from alkyl, each R' is independently selected from hydrido, alkyl, or halogen, and R" is selected from hydrido or methyl.

Preferred organic cations include 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium, N-ethylpyridinium, N-butylpyridinium, N-hexylpyridinium, 4-methyl-N-butyl-pyridinium, 3-methyl-N-butyl-pyridinium, 4-methyl-N-hexyl-pyridinium, 3-methyl-N-hexyl-pyridinium, 4-methyl-N-octyl-pyridinium, 3-methyl-N-octyl-pyridinium, 3,4-dimethyl-N-butyl-pyridinium, and 3,5-dimethyl-N-butyl-pyridinium.

Preferred anions of the ionic liquid are chloride (Cl$^-$), bromide (Br$^-$), tetrafluoroborate ([BF$_4$]$^-$), hexafluorophosphate ([PF$_6$]$^-$), [SbF$_6$]$^-$, [CuCl$_2$]$^-$, [AlCl$_4$]$^-$, [Al$_2$Cl$_7$]$^-$, [Al$_3$Cl$_{10}$]$^-$, methylsulfate (CH$_3$SO$_4^-$), trifluoroacetate (CF$_3$CO$_2^-$), heptafluorobutanoate (CF$_3$(CF$_2$)$_2$CO$_2^-$), triflate (CF$_3$SO$_2^-$), nonaflate (C$_2$F$_5$SO$_2^-$), bis(trifluoromethylsulfonyl)imide ((CF$_3$SO$_2$)$_2$N$^-$), bis(perfluoroethylsulfonyl)imide ((C$_2$F$_5$SO$_2$)$_2$N$^-$), and tris(trifluoromethylsulfonyl)methide ((CF$_3$SO$_2$)$_3$C$^-$). Ionic liquids are available from Covalent Associates (Woburn, Mass.), Solvent Innovation (Köln, Germany), Aldrich Chemical Company (Milwaukee, Wis.), and Acros Organics (Geel, Belgium).

In one embodiment, to perform the coupling reaction, at least one of the chemical species having a nucleoside moiety is dissolved in a solution having at least 98 percent by weight of ionic liquid, whereupon the other chemical specie having a nucleoside moiety (the second nucleoside moiety) is contacted with the solution containing ionic liquid and the first nucleoside moiety. In other embodiments, the solution has at least about 90% ionic liquid, or at least about 75% ionic liquid, or at least about 50% ionic liquid, or at least about 25% ionic liquid, or at least about 10% ionic liquid. Co-solvents that may be mixed into the ionic liquid include but are not limited to acetoiiitrile, tetrahydroflirati, dimetilylformamide, methylene chloride, propylene carbonate, adiponitrile, toluerie, dioxane, dimethylsulfoxide, and N-methyl pyrrolidone. An activator compound is typically included in a concentration of about 0.05 molar up to about 0.5 molar. The activator is generally tetrazole, S-ethyl-thiotetrazole, 4-nitrotriazole, or dicyanoimidazole, although other, acidic azoles may be used. One potential advantage of using an ionic liquid is that the ionic liquid may serve as the activator.

In the conventional synthesis method depicted schematically in FIG. 1, it is typical to use an aqueous solution of iodine for the oxidation step. However, phosphoramidite reagents that have been activated for coupling are highly reactive with water. The invention may be extended to include using ionic liquids as solvents elsewhere in the synthesis cycle to reduce or substantially eliminate the presence of water during oxidation and deprotection.

In one embodiment of the invention, the first nucleoside moiety is a monomer nucleoside phosphoramidite, which is coupled to a free hydroxyl of a second nucleoside moiety, analogous to conventional polynucleotide synthesis. The invention also encompasses the formation of an internucleoside bond between two polynucleotides or oligonucleotides, or between a polynucleotide and an oligonucleotide. In such case, the first nucleoside moiety corresponds to the one of the polynucleotides or oligonucleotides, and the second polynucleotide moiety corresponds to the polynucleotide or oligonucleotide to be joined to the first nucleoside moiety. The skilled practitioner in the art will realize that one of the nucleoside moieties must be activated, as in a phosphoramidite. Such modification is well known in the art.

As explained earlier herein, the method of the invention also lends itself to synthesis of polynucleotides in the 5'-to-3' direction. In such a case, the initial step of the synthetic process involves attachment of an initial nucleoside to a solid support at the 5' position, leaving the 3' position available for covalent binding of a subsequent monomer. The coupling reaction in which the nucleoside monomer becomes covaleritly attached to the 3' hydroxyl moiety of the support bound nucleoside is conducted under reaction conditions identical to those described for the 3'-to-5' synthesis. The synthesis cycle is then continued with the (optional) capping step, the oxidation of the internucleotide bond, and the deprotection of the active site hydroxyl in preparation for the next synthesis cycle, which is repeated until a polynucleotide having the desired sequence and length is obtained. Following synthesis, the polynucleotide may, if desired, be cleaved from the solid support. The details of the synthesis in the 5'-to-;3' direction will be readily apparent to the skilled practitioner based on the prior art and the disclosure contained herein.

The coupling reaction as described herein may easily be adapted to be performed in a conventional automated oligonucleotide synthesizer utilizing an insoluble substrate to immobilize the polynucleotides during synthesis. Such methodology will be apparent to those skilled in the art and is described in the pertinent texts and literature, e.g., in D. M. Matteuci et al. (1980) Tet. Lett. 521:719 and U.S. Pat. No. 4,500,707. Examples of suitable support materials include, but are not limited to, polysaccharides such as agarose (e.g., that available commercially as Sepharose®, from Pharmacia) and dextran (e.g., those available commercially under the tradenames Sephadex® and Sephacyl®, also from Pharmacia)

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method of forming an internucleotide bond comprising contacting a free hydroxyl of a growing polynucleotide with a solution comprising a nucleotide monomer and at least 50% by weight of an ionic liquid.

2. The method of claim 1 wherein the solution includes at least 75% by weight of an ionic liquid.

3. The method of claim 1 wherein the solution includes at least 90% by weight of an ionic liquid.

4. The method of claim 1 wherein the solution includes at least 98% by weight of an ionic liquid.

5. The method of claim 1 wherein the ionic liquid is an organic salt comprising a substituted heterocyclic organic cation.

6. The method of claim 5 wherein the organic salt further comprises an anion selected from chloride ($Cl^-$), bromide ($Br^-$), tetrafluoroborate ($[BF_4]^-$), hexafluorophosphate ($[PF_6]^-$), $[SbF_6]^-$, $[CuCl_2]^-$, $[AlCl_4]^-$, $[Al_2Cl_7]^-$, $[Al_3Cl_{10}]^-$, methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), bis(trifluoromethylsulfonyl)imide ($(CF_3SO_2)_2N^-$), bis(perfluoroethylsulfonyl)imide ($(C_2F_5SO_2)_2N^-$), and tris(trifluoromethylsulfonyl)methide ($(CF_3SO_2)_3C^-$).

7. The method of claim 5 wherein the organic salt is characterized as being a liquid when being >98% pure and at standard temperature and pressure.

8. The method of claim 1 wherein the organic salt is characterized as being liquid below 80° C. at standard atmospheric pressure.

9. The method of claim 5 wherein the cation is an N-substituted pyridine having the formula

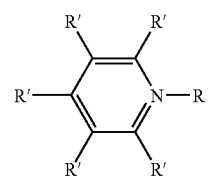

wherein R is alkyl and each R' is independently selected from hyrido, alkyl, or halogen group.

10. The method of claim 5 wherein the cation has the formula

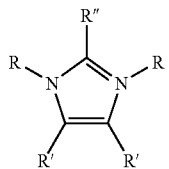

wherein each R is independently selected from alkyl, each R' is independently selected from hydrido, alkyl, or halogen, and R" is selected from hydrido or methyl.

11. The method of claim 1 wherein the ionic liquid is an organic salt comprising a cation selected from an N-substituted pyridine and a 1,3-disubstituted imidazole.

12. A method of forming an internucleotide bond between a first nucleoside moiety and a second nucleoside moiety, the method comprising
   (a) dissolving the first nucleoside moiety in a solution comprising at least 50% by weight of an ionic liquid, and
   (b) contacting the second nucleoside moiety with the product of (a) to form the internucleotide bond.

13. The method of claim 12 wherein the solution includes at least 75% by weight of an ionic liquid.

14. The method of claim 12 wherein the solution includes at least 90% by weight of an ionic liquid.

15. The method of claim 12 wherein the solution includes at least 98% by weight of an ionic liquid.

16. The method of claim 12, further comprising
   (c) contacting the internucleotide bond with an oxidizing reagent to oxidize the internucleotide bond.

17. The method of claim 12 wherein the second nucleoside moiety is immobilized on a solid support.

18. The method of claim 12 wherein the ionic liquid is an organic salt comprising a substituted heterocyclic organic cation.

19. The method of claim 18 wherein the organic salt further comprises an anion selected from chloride (Cl$^-$), bromide (Br$^-$), tetrafluoroborate ([BF$_4$]$^-$), hexafluorophosphate ([PF$_6$]$^-$), [SbF$_6$]$^-$, [CuCl$_2$]$^-$, [AlCl$_4$]$^-$, [Al$_2$Cl$_7$]$^-$, [Al$_3$Cl$_{10}$]$^-$, methylsulfate (CH$_3$SO$_4$$^-$), trifluoroacetate (CF$_3$CO$_2$$^-$), heptafluorobutanoate (CF$_3$(CF$_2$)$_2$CO$_2$$^-$), triflate (CF$_3$SO$_2$$^-$), nonaflate (C$_2$F$_5$SO$_2$$^-$), bis(trifluoromethylsulfonyl)imide ((CF$_3$SO$_2$)$_2$N$^-$), bis(perfluoroethylsulfonyl)imide ((C$_2$F$_5$SO$_2$)$_2$N$^-$), and tris(trifluoromethylsulfonyl)methide ((CF$_3$SO$_2$)$_3$C$^-$).

20. The method of claim 18 wherein the organic salt is characterized as being a liquid when being >98% pure and at standard temperature and pressure.

21. The method of claim 18 wherein the cation is an N-substituted pyridine having the formula

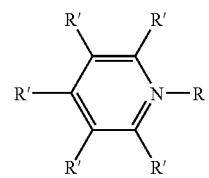

wherein R is alkyl and each R' is independently selected from hyrido, alkyl or halogen group.

22. The method of claim 18 wherein the cation has the formula

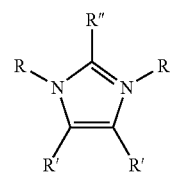

wherein each R is independently selected from alkyl, each R' is independently selected from hydrido, alkyl, or halogen, and R" is selected from hydrido or methyl.

23. The method of claim 12 wherein the ionic liquid is an organic salt comprising a cation selected from an N-substituted pyridine and a 1,3-disubstituted imidazole.

24. The method of claim 12 wherein the organic salt is characterized as being liquid below 80° C. at standard atmospheric pressure.

* * * * *

UNITED STATES PATENT AND TRADEMARK OFFICE
CERTIFICATE OF CORRECTION

PATENT NO. : 7,411,061 B2  Page 1 of 1
APPLICATION NO. : 11/020408
DATED : August 12, 2008
INVENTOR(S) : Myerson et al.

It is certified that error appears in the above-identified patent and that said Letters Patent is hereby corrected as shown below:

On the title page, item (56), under "Other Publications", in column 2, line 14, delete "ethoxcarbonyl;" and insert -- ethoxycarbonyl; --, therefor.

On the title page, item (56), under "Other Publications", in column 2, line 15, delete "Ologodeoxyribonucleotide" and insert -- Oligodeoxyribonucleotide --, therefor.

On the title page, item (56), under "Other Publications", in column 2, line 19, delete "Doxynucleoside" and insert -- Deoxynucleoside --, therefor.

On the title page, item (56), under "Other Publications", in column 2, line 34, delete ""Sunthesis" and insert -- "Synthesis --, therefor.

On the title page item (56), under "Other Publications", in column 2, line 34, delete "Raioiodination" and insert -- Radioiodination --, therefor.

In column 12, line 65, in Claim 9, delete "hyrido," and insert -- hydrido, --, therefor.

In column 13, line 17, in Claim 12, delete "intemucleotide" and insert -- Internucleotide --, therefor.

In column 14, line 21, in Claim 21, delete "hyrido," and insert -- hydrido, --, therefor.

In column 14, line 21, in Claim 21, after "alkyl" insert -- , --.

Signed and Sealed this

Twenty-fourth Day of February, 2009

JOHN DOLL
*Acting Director of the United States Patent and Trademark Office*